United States Patent [19]
Bühring

[11] Patent Number: 5,808,002
[45] Date of Patent: Sep. 15, 1998

[54] STEM CELL FACTOR RECEPTOR-(C-KIT)-SPECIFIC MONOCLONAL ANTIBODY A3C6E2

[75] Inventor: Hans-Jörg Bühring, Tübingen, Germany

[73] Assignee: Eberhard-Karls-Universität Tubingen, Tubingen, Germany

[21] Appl. No.: 778,524

[22] Filed: Jan. 3, 1997

[30] Foreign Application Priority Data

Jan. 10, 1996 [DE] Germany ............... 196 00 589.2

[51] Int. Cl.$^6$ ............... C07K 16/28; C12N 5/20; A61K 39/395; C12Q 33/577
[52] U.S. Cl. ............... 530/388.22; 530/358.7; 530/391.3; 530/391.7; 424/144.1; 424/178.1; 435/7.24; 435/34; 435/334; 435/343; 435/343.1; 435/346; 435/377; 435/372.3; 436/538
[58] Field of Search ............... 530/388.22, 388.7, 530/391.3, 391.7; 424/144.1, 178.1; 435/334, 343, 343.1, 7.24, 346, 376, 377, 372, 372.3, 34; 436/538

[56] References Cited

U.S. PATENT DOCUMENTS 5,489,516  2/1996  Broudy et al. ............... 435/7.23
5,545,533  8/1996  Bartke et al. ............... 435/7.23

FOREIGN PATENT DOCUMENTS

WO92/17505  10/1992  WIPO ............... C07K 15/28
WO 92/21766  12/1992  WIPO .

OTHER PUBLICATIONS

Blechmann, J. et al.: "Soluble c–Kit Proteins and Antireceptor Monoclonal Antibodies Confine the Binding Site of the Stem Cell Factor"; *J. Biological Chemistry*, vol. 268 No. 6 Issue of Feb. 25, pp. 4399–4406 (1993).

Morita, S. et al.: "Isolation and Characterization of Two Monoclonal Antibodies that Recognize Different Epitopes of the Human c–kit Receptor", *Tohaku J. Exp. Med.*, pp. 178, 187–198 (Feb. 1996).

Bühring, H. et al.: "Leucocyte Typing V, CR2.7 Stem–Cell Factor Receptor (p145(c–kit) Summary Report (CD117)", *Oxford University Press*, pp. 1882–1888 (1995).

Zsebo, K. et al.: "Stem Cell Factor Is Encoded at the Sl Locus of the Mouse and is the Ligand for the C–kit . . . ", *Cell* vol. 63, pp. 213–224 (1990).

Bühring, H. et al.: "The Monoclonal Antibody 11G7 Recognizes a Novel Differentiation Antigen Expressed . . . ", *Hybridoma* vol. 10, No. 1, pp. 77–88 (1991).

Matsuo, Y. et al.: "Establishment and Characterization of a Novel Megakaryoblastoid Cell Line . . . "; *Human Cell* 4, pp. 261–264 (1991).

*Primary Examiner*—David L. Fitzgerald
*Attorney, Agent, or Firm*—Claude A.S. Hamrick

[57] ABSTRACT

The present invention relates to a monoclonal antibody that binds specifically to a human stem cell factor (SCF) receptor. The invention further relates to hybridoma cells that produce such an antibody, and to a method for generating such hybridoma cells.

22 Claims, 2 Drawing Sheets

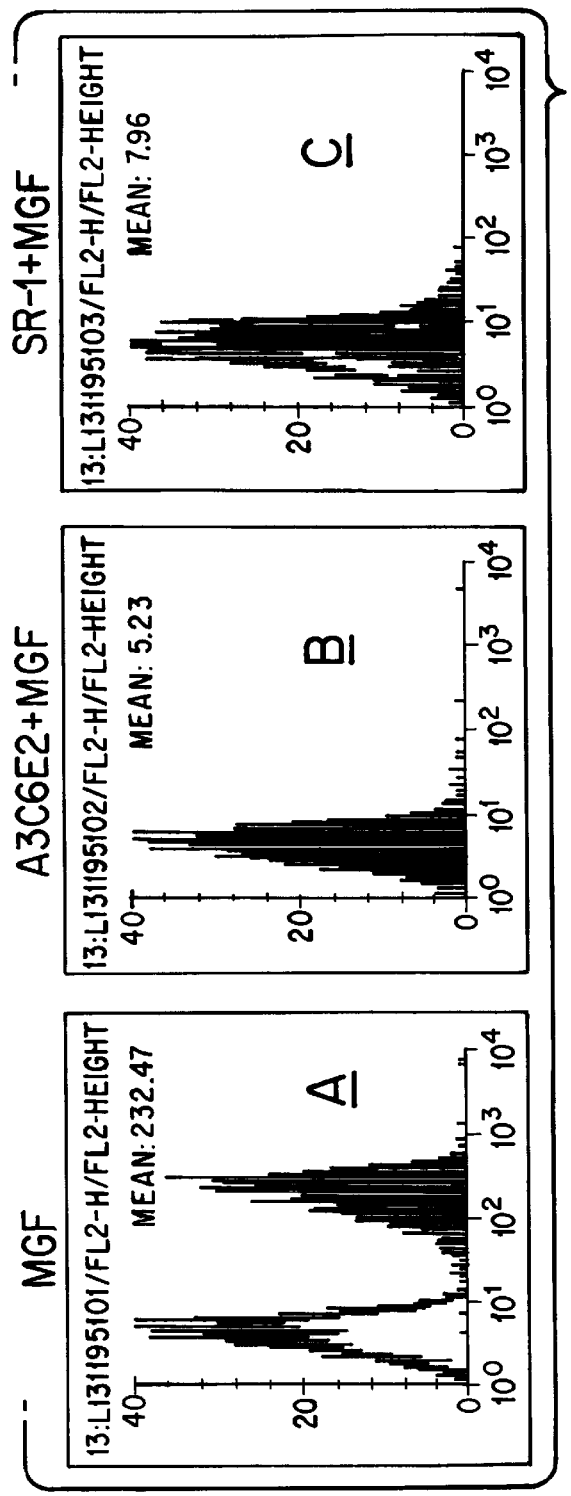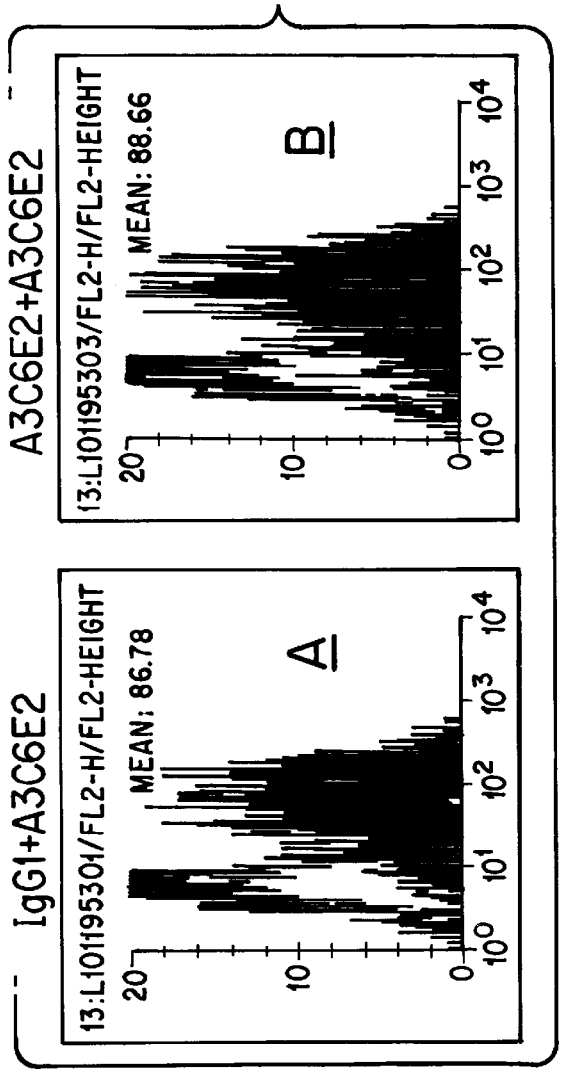

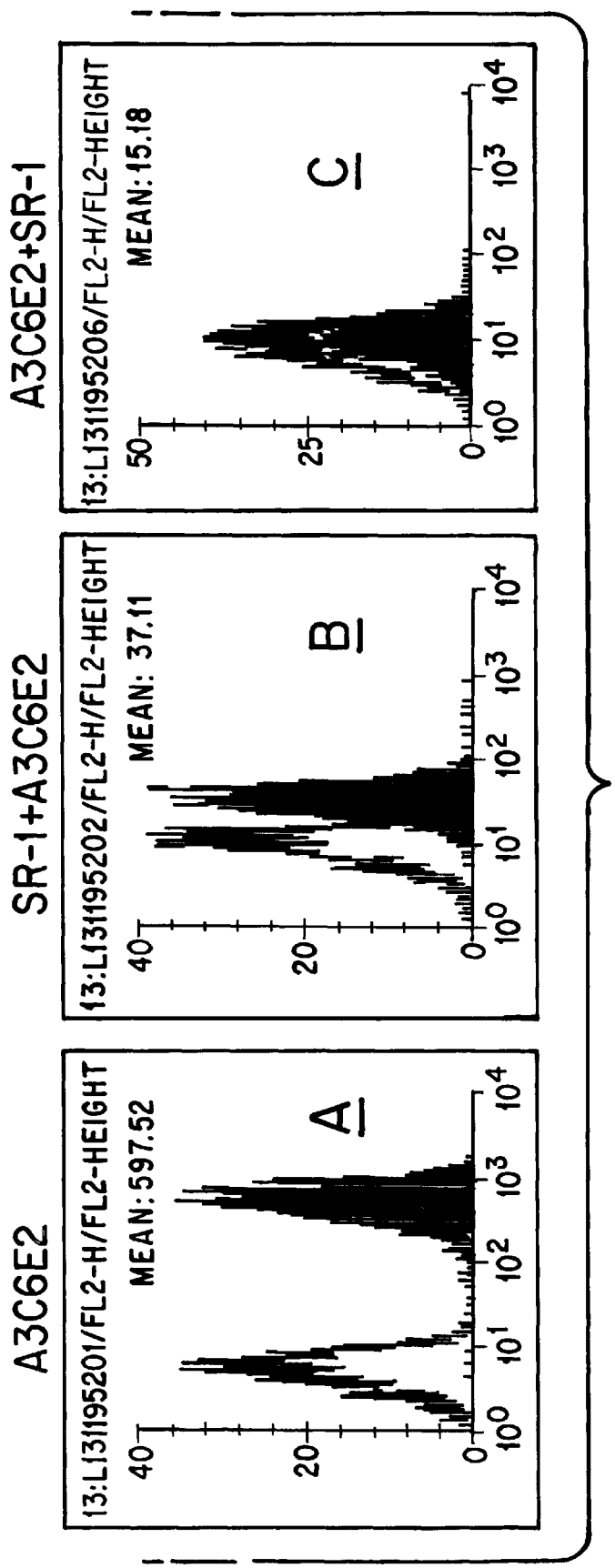
Fig_3

STEM CELL FACTOR RECEPTOR-(C-KIT)-SPECIFIC MONOCLONAL ANTIBODY A3C6E2

BACKGROUND OF THE INVENTION

1. Field of the Invention

The invention relates to a monoclonal antibody that binds specifically to a human stem cell factor (SCF) receptor.

The stem cell factor (SCF) is a growth factor that stimulates the proliferation of pluripotent hematopoietic blood stem cells. It interacts with a receptor, namely the CD117 protein (synonyms: SCF receptor or c-kit receptor [Bühring et al. in Schlossman et al., (Eds), Leucocyte Typing V, Oxford University Press, Oxford 1995, pp. 1882–1888]), which is localized in the plasma membrane of blood stem cells and is encoded by the proto-onkogen c-kit (Zsebo et al., Cell 63: 213–224, 1990).

SCF as such is produced and secreted by different natural cells, and meanwhile has become commercially available as a gene technologically generated recombinant product of, for example, E. coli.

Blood stem cells are undifferentiated progenitor cells, capable of unlimited division, from which various highly specialized blood cell types develop. They are responsible for the natural, constant regeneration of those different blood cell types, and play an important role in the formation and development of blood cell diseases, in particular anemia, leukemia and lymphoma. In addition, they are a preferred target for diagnosis and therapeutic treatment of such diseases.

The specific identification, isolation and modulation of the blood stem cells is, consequently, of elementary importance for the desired rapid and reliable diagnosis and for an effective, targeted therapy of blood cell diseases.

Looking for a mediator for such a specific cellular treatment, one would, above all, consider an antibody that binds specifically to blood stem cells. An antibody that recognizes the SCF receptor protein CD117 as an antigen is, therefore, especially well suited, CD117 being expressed on stem cells.

Such an antibody may be coupled to simple indicator reagents, such as fluorescent dyes or radioactive substances, and to special, therapeutically effective reagents.

Since polyclonal antibodies are available only to a limited extent and cannot be reproduced identically, the antibody should be a monoclonal antibody.

2. Description of the Related Art

WO 92/17505 describes the only blocking monoclonal antibody known to this day that binds to the stem cell factor receptor (SCF-R). This antibody, named SR-1, binds specifically to the CD117 protein, thereby blocking SCF binding to that receptor. The antibody SR-1 belongs to isotype IgG 2A.

The antibody SR-1 provides on the one hand a very effective means for identifying and modulating blood stem cells and, thus, for diagnosis and therapy of blood cell diseases. On the other hand, the previous unique character of this antibody means that a real control of the results achieved with it, by parallel tests with a comparable blocking monoclonal antibody of the same or a very similar specificity, was never possible.

SUMMARY OF THE INVENTION

It is therefore the object of the present invention to provide at least one additional blocking monoclonal antibody that binds specifically to the human SCF receptor protein CD117.

This object is achieved by providing a monoclonal antibody that is produced and released by hybridoma cells that were deposited on Dec. 19, 1995, under No. DSM ACC 2247, at the Deutsche Sammlung von Mikroorganismen und Zellkulturen GmbH, DSM, in accordance with the Budapest Agreement. The antibody has been given the designation A3C6E2. It belongs to isotype IgG 1 and is capable of blocking SCF molecules from binding to the SCF receptor.

With the antibody according to the invention, a second monoclonal antibody has been provided that can be reproduced in a standardized manner and can thus potentially be produced in unlimited amounts and that binds specifically to the SR-1 epitope on the SCF receptor protein CD117 of human blood stem cells.

The antibody according to the invention permits cells, that have an extracellular domain of the SCF receptor protein CD117, to be identified and modulated in a specific way. It therefore provides to physicians and research personnel an alternative means to the known antibody SR-1, for on the one hand detecting such cells, both in cell culture and in the patient's organism, and on the other hand manipulating such cells, if desired, either by means of the antibody as such, or by specific reagents coupled to it.

By making available this antibody directed against the SCF receptor protein CD117, according to the invention, it has become possible for the first time to effectively control the test results obtained with the known antibody and to significantly improve the safety of their evidence. The same applies of course in the reverse case, when the antibody according to the invention is used as a primary test antibody, and the antibody SR-1 serves as control antibody.

The present invention further relates to hybridoma cells that produce a monoclonal antibody directed against the human SCF receptor protein CD117. It comprises especially the hybridoma cells that have been deposited, under No. DSM ACC 2247, at the Deutsche Sammlung von Mikroorganismen und Zellkulturen GmbH, DSM, Mascheroder Weg 1 b, D-38124 Braumschweig, Germany,in accordance with the Budapest Agreement, and that produce the antibody named A3C6E2.

The invention further relates to a method generating hybridoma cells that synthesize and release an antibody directed against the human SCF receptor protein CD117. The method comprises the steps generally known in the art, as described for example by Bühring et al. in Hybridoma 1991, Vol. 10, No. 1, pp. 77–78:

1. Immunizing or sensitizing an animal, preferably a mouse of the Balb/c line, with the antigen and/or the immunogen,
2. collecting the antibody-producing cells, preferably the lymphozytes of the spleen of that animal;
3. fusing those antibody-producing cells with a stable, immortalized cell line, preferably a myeloma cell line, to form hybridoma cells; and
4. isolating and cloning such hybridoma cells that secrete an antibody binding to the antigen.

The method according to the invention is characterized by the fact that the animal is immunized with cells of the undifferentiated, megakaryoblastoid cell line MOLM-1.

It proved to be an advantage in this connection that this cell line shows a strong expression of SCF receptor protein CD117, as was found out during the tests that led to the antibody A3C6E2.

When screening hybridoma cells which produce stem cell-specific antibodies, it is preferred during isolation of the hybridoma cells, if those hybridoma cells are selected which produce antibodies having a specificity against bone marrow cells, it being further preferred if only those hybridoma cells are tested for the specificity for bone marrow cells of the corresponding antibodies for which hybridoma cells it has been shown previously that their antibodies show only weak or, preferably, negative reaction with peripheral blood cells.

This screening makes use of the fact that the bone marrow shows a pronounced presence of undifferentiated cells, including hematopoietic stem cells that comprise the antigen to be recognized by the antibody. A preliminary test for negative reaction with peripheral blood cells makes it possible, in a rapid and simple way and without having to test great numbers of cells in vain, to collect those antibodies that bind selectively to the antigens characteristic for bone marrow cells and are not, or only poorly expressed on peripheral blood cells. To say it in other words: The specificity in selecting stem cell-specific antibodies is increased notably and in a simple way by this screening method.

During the further screening process one preferably selects those hybridoma cells that produce an antibody that binds specifically to fibroblasts transfected with the human c-kit gene.

An alternative, or supplementary screening method consists in selecting such hybridoma cells that produce an antibody that prevents the binding of SCF molecules to the blood stem cells, i.e. to the SCF receptor protein CD117.

Other screening methods, such as the immune precipitation of radioactively labeled purified SCF receptor protein, or the enzyme linked immunosorbent assay, shortly ELISA, are of course also possible. The SCF employed in such tests may come from different kinds of mammals, although a human SCF, especially a recombinant SCF, for example from *E. coli*, is preferred.

The invention further relates to the use of a monoclonal antibody named A3C6E2, as produced and released by the hybridoma cells deposited, under No. DSM ACC 2247, at the Deutsche Sammlung von Mikroorganismen und Zellkulturen GmbH, DSM, for the diagnosis of malignant blood cells, i.e. of cancer of the blood, especially of leukemia and lymphoma.

One makes use in this case of the fact that the tumor cells differ from healthy blood cells by the number of SCF receptor molecules in the cell membrane. An antibody according to the invention, coupled to an indicator, for example a radioactive marker, binds this indicator agent indirectly to these cells thereby permitting the indirect identification of those cells, for example by x-ray diagnostic/szintigraphic methods. This permits a very early diagnosis of tumors, even in-vivo.

As the antibody according to the invention binds to the receptor for the SCF and, thus, to a protein that plays a central role in regulating the cell proliferation, it offers a direct point of attack for manipulation, especially for the inhibition of cell multiplication.

The present invention, therefore, also relates to the use of the monoclonal antibody A3C6E2, as produced and released by the hybridoma cells deposited, under No. DSM ACC 2247, at the Deutsche Sammlung von Mikroorganismen und Zellkulturen GmbH, DSM, for the therapeutic treatment of malignant blood cells. The antibody may be coupled, according to the invention, to a therapeutically active agent, thereby enabling the tumor cells to be modulated or even eliminated directly and in a specific way.

In order to facilitate the therapeutic and/or diagnostic application of the antibody according to the invention, the antibody should be mixed in a pharmaceutical composition with adequate accessory substances. Consequently, the invention also relates to a pharmaceutical agent for diagnostic treatment, and to a pharmaceutical agent for the therapeutic treatment of malignant blood cells, each containing an antibody A3C6E2 of the kind produced and released by the hybridoma cells deposited, under No. DSM ACC 2247, at the Deutsche Sammlung von Mikroorganismen und Zellkulturen GmbH, DSM.

In the pharmaceutical agent the antibody A3C6E2 may be coupled to a special diagnostic agent and/or therapeutical agent directed against the leukemia cells and/or the lymphoma cells.

The invention further relates to the use of an antibody according to the invention for detecting and/or isolating hematopoietic cells, and to a corresponding method. The method for detecting and/or isolating hematopoietic cells comprises the steps of:

1) Incubating a cell suspension containing hematopoietic cells with an antibody that binds to hematopoietic cells; and 2) separating the cells bound to the antibody from the remaining cells;

and is characterized in that the antibody is the monoclonal antibody A3C6E2 according to the invention.

The separation is carried out preferably by fluorescence-activated cell sorting (FACS), by column chromatography or by direct immune adherence.

In the case of fluorescence-activated cell sorting (FACS), the cells carrying the SCF receptor are mixed with the monoclonal antibody A3C6E2 according to the invention, after the latter has been coupled directly or indirectly to a fluorescence dye, such as fluorescein isothiocyanate (FITC) or phycoerythrin (PE). The fluorescence-labeled cells can then be sorted by the degree of fluorescence radiation using the known sorting techniques.

The isolation method according to the invention can be used in particular in connection with the transplantation of bone marrow for the purpose of isolating healthy hematopoietic stem cells from any tumor cells present, and for purifying in this way the bone marrow to be transplanted. The reinfection risk of the patient is thereby notably reduced, above all in the case of autotransplantation (autologous transplantation) following chemotherapy or radiotherapy.

In order to be able to carry out the detection and/or isolating process quickly and without lengthy preparations, the invention provides for a corresponding kit containing the antibody A3C6E2 according to the invention.

The cells obtained by the isolation method according to the invention, which are thereby simultaneously purified, may be further subfractioned in order to obtain even more homogeneous cell populations. Such subfractioning may be carried out, for example, with the aid of monoclonal antibodies directed against an antigen that occurs only in one subpopulation of the cells carrying the SCF receptor. The cell surface protein CD34 is an example of such an antigen.

The hematopoietic cells isolated and purified according to the invention are especially well suited for a gene therapy treatment that comprises retrovirally induced gene transfer into the hematopoietic cells.

The invention further relates to the use of the antibody A3C6E2 according to the invention for inhibiting hematopoiesis. This may be carried out either in cell culture in the test laboratory, or in patients in the medical practice. For an application in a patient, the antibody according to the invention should be mixed with accessory substances that facilitate its application. The invention therefore also relates to a pharmaceutical agent for inhibiting hematopoiesis, that contains the antibody in a quantity that inhibits the SCF.

It is known that many neoplastic cells differ from normal, i.e. healthy, cells also by the fact that they do not express any SCF receptor molecules on the cell surface.

The invention, therefore, also relates to a method for separating normal cells from neoplastic leukemia cells, comprising the basic steps of:

1) Incubating a mixture of normal cells and neoplastic leukemia cells with an antibody; and
2) separating the hematopoietic cells from the neoplastic leukemia cells, according to the different numbers of SCF receptors on the plasma membrane of the hematopoietic cells on the one hand and the neoplastic leukemia cells on the other hand.

The method according to the invention is characterized by the fact that the antibody is the monoclonal antibody A3C6E2.

The separation may be carried out for example by initially labeling the cells in the mixture with the antibody according to the invention, coupling them thereafter to a biotinized antibody directed against the donor organism of the antibody A3C6E2, and passing them finally through an avidin column. Cells having a higher number of SCF receptor molecules will be retained in the column, while cells without SCF receptors will pass through the column. Alternative separating methods that may be used are direct immune adherence, fluorescence-activated cell sorting (FACS) and magnetically activated cell sorting (MACS).

The present invention also relates to a method for detecting SCF receptors in a cell sample. The method comprises the basic steps of:

1) Incubating a cell sample with an antibody; and
2) detecting the antibody bound to the SCF receptor;

and is characterized by the fact that the antibody is the monoclonal antibody A3C6E2.

The cell sample may consist of normal cells and/or leukemia cells and/or lymphoma cells. Detecting the bound antibody is carried out, preferably, by means of a marker coupled to the antibody A3C6E2.

The method according to the invention renders it possible, for example, to test a blood sample or tissue sample of a patient who is suspected to suffer from a tumor disease, for presence of any neoplastic or lymphoma cells.

The invention also relates to the use of the antibody A3C6E2 as produced and released by the hybridoma cells deposited, under No. DSM ACC 2247, at the Deutsche Sammlung von Mikroorganismen und Zellkulturen GmbH, DSM, for modifying the sensitivity of patients to cell cycle-specific chemotherapeutic agents.

By administering the antibody according to the invention in a quantity that limits or completely abolishes the binding of SCF to its receptor, one inhibits the growth and the development of the cells carrying the SCF receptor.

In order to facilitate the administration of the antibody according to the invention, the antibody should be mixed in a pharmaceutical composition with adequate accessory substances. The invention, therefore, also relates to a pharmaceutical agent for modifying the sensitivity of patients to cell cycle-specific chemotherapeutic treatments, that contains the antibody A3C6E2 as produced and released by the hybridoma cells deposited, under No. DSM ACC 2247, at the Deutsche Sammlung von Mikroorganismen und Zellkulturen GmbH, DSM.

The respective pharmaceutical agent should contain the antibody in a quantity that inhibits the binding and/or the production of SCF.

Further advantages can be taken from the following description.

It is understood that the afore-mentioned features and those to be explained in the following can be used not only in the specific combinations, but also in other combinations or alone without going beyond the scope of the present invention.

BRIEF DESCRIPTION OF THE DRAWINGS

The invention will be described hereafter with reference to certain exemplified applications and embodiments, in combination with the drawings, in which:

FIGS. 1A–C show three histograms of flow cytometer measurements (examination of the degree of blocking of biotinized ligands) on M07e cells, 1A showing the case where the cells were incubated only with the ligand (biotinized SCF+SA-PE), 1B showing the case where the cells were pre-incubated with the antibody A3C6E2 and then incubated with the ligand, and 1C showing the case where the cells were pre-incubated with the comparative antibody SR-1 and then incubated with the ligand;

FIGS. 2A–B show two histograms of flow cytometer measurements (examination of the down regulation of the receptor) on M07e cells, 2A showing the case where the cells were pre-incubated with an IgG1 control antibody and then incubated with the antibody A3C6E2 and an anti-IgG1-PE antiserum, and 2B showing the case where the cells were pre-incubated with the antibody A3C6E2 and then incubated with the same antibody and an anti-IgG1-PE antiserum; and FIGS. 3A–C show three histograms of flow cytometer measurements (epitope analysis) on M07e cells, 3A showing the case where the cells were incubated with the antibody A3C6E2 and labeled with an anti-IgG1-PE antiserum, 3B showing the case where the cells were pre-incubated with the comparative antibody SR-1 and then further incubated and labeled as in the case of 3A, and 3C showing the case where the cells were incubated initially with the antibody A3C6E2 and then incubated with the comparative antibody SR-1 and labeled with an anti-IgG2A-PE antiserum.

DETAILED DESCRIPTION OF THE EMBODIMENTS OF THE INVENTION

EXAMPLE 1

Establishment and characterization of monoclonal antibodies to the SCF receptor protein CD117

Cells of the undifferentiated megakaryoblastoid cell line MOLM-1 are used as an antigen (Matsuo A, Adachi T, Tsubota T, Imanishi J, Minowada J. Establishment and characterization of a novel megakaryoblastoid cell line, MOLM-1, from a patient with chronic myelogenous leukemia. Human Cell 1991; 4: 261–264).

Eight weeks old Balb/c mice are immunized intraperitoneally twice, at intervals of 10 days, with $10^7$ cells of the cell line MOLM-1. Four days before the fusion, $5\times10^5$ cells are administered directly into the spleen in order to reinforce the immune response.

The formation of antibodies in the organism of the mouse is tested by screening the blood serum of the respective animal for binding properties with the antigen using the ELISA test well-known to any man skilled in the art.

Approximately 3 weeks later, the lymphozytes of the successfully immunized animal are collected by removing the animal's spleen and disintegrating it into a cell suspension.

The suspended spleen cells are fused with myeloma cells of the known line SP2/0 in the presence of polyethylene glycol. The fusion culture is cultivated in a medium containing hypoxanthine, aminopterin and thymidine (HAT), here in HAT-RPMI-1640, in which only hybrid cells can grow as these have both the property of myeloma cells to divide infinitely, and the property of the antibody-producing lymphozytes to grow in a medium containing HAT.

Following fusion, the cells are spread in microtiter plates and are incubated at 37° C. in the presence of 5% $CO_2$.

The culture supernatant is screened in a flow cytometer after 10–14 days on the MOLM-1 cell line. In a second step, the supernatants are tested for reactivity with peripheral blood cells, as these do not express selective stem cell antigens. Any supernatant showing a negative or weak reaction with peripheral blood cells are tested for reactivity with bone marrow cells afterwards. Any hybridoma producing antibodies with a specificity for bone marrow cells are selected and isolated and cultivated, i.e. cloned, by the known limited dilution method.

This screening strategy benefits from the fact that a large number of undifferentiated cells, including hematopoietic stem cells, is found in the bone marrow.

Positively reacting hybridoma cell cultures are subjected to further cultivation, the antibodies are concentrated, purified and characterized.

The monoclonal antibody A3C6E2 was obtained by the screening strategy described above. The isotype was determined to be IgG1, through PE-conjugated anti-isotype-specific antisera, by direct immune fluorescence.

Production, purification and characterization of the antibody were carried out by the methods generally known in the art.

The antibody A3C6E2 produced by the hybridoma cells deposited, under No. DSM ACC 2247, at the Deutsche Sammlung von Mikro-organismen und Zellkulturen GmbH, DSM, exhibits the following characteristic features:

Immunoglobulin class: IgG1

Specific binding affinity to: CD117

EXAMPLE 2

Identification of the antigen recognized by the monoclonal antibody A3C6E2.

Identification of the antigen was carried out by binding tests using mouse cells with and without human SCF receptors (transfectants).

A sample (A) containing mouse fibroblasts of the cell line NIH-3T3/hc-kit transfected with the human c-kit gene (Yardmen et al., EMBO J. 6: 3341, 1987) was incubated with the antibody A3C6E2 according to the invention.

As a control, a sample (B) containing mouse fibroblasts of non-transfected cell line NIH-3T3 was equally incubated with the antibody A3C6E2, in the same concentration as sample (A).

Both samples were labeled with an anti-IgG1-PE antiserum and then analyzed in a flow cytometer.

Binding of the antibody A3C6E2 could be shown exclusively for sample (A). This means that the antibody A3C6E2 according to the invention bound specifically to those cells that contain the c-kit gene and that, consequently, express the SCF receptor.

EXAMPLE 3

Identification of the monoclonal antibody A3C6E2 as an antibody with antagonistic (ligand blocking) but no agonistic (ligand stimulating) effect.

For blocking the ligand binding, a sample (1A) of M07e cells was incubated with the biotinized ligand MGF-biotine (MGF-b==kit ligand) in a concentration of 200 ng/ml, and was then labeled with SA-PE (positive control).

A second sample (1B) of M07e cells was initially pre-incubated for 30 minutes with the antibody A3C6E2, in a concentration of 7 µg/ml, and then treated the same way as sample (1A).

Both samples were analyzed in the flow cytometer. The results are illustrated in FIG. 1A and FIG. 1B.

As a comparative test, a third sample (1C) of M07e cells was treated the same way as sample (A) with the difference that the known antibody SR-1 was used in a concentration of 10 µg/ml instead of the antibody A3C6E2 according to the invention.

As can be seen in the histogram of FIG. 1, the antibody A3C6E2 according to the invention blocks the binding of the ligand to a degree of 99.99%, the comparative antibody SR-1 blocks the combination to a degree of 98.7%.

In the case of tyrosine kinase receptors, such as the SCF receptor, receptor activation initiated by the binding of the ligand will initially lead to the formation of receptor dimer complexes and their internalization into the cell. Some antibodies can simulate the ligand, which means that they act as agonists, and will therefore also result in such a receptor dimer formation and internalization (Bühring et al., Cancer Res. 53: 4424, 1993).

A sample (2A) of MOLM-1 cells was pre-incubated for 2 hrs., at 37° C., with a control IgG1 antibody, then incubated with the antibody A3C6E2 according to the invention and finally incubated with anti-IgG1-PE antiserum.

A second sample (2B) was initially incubated with the antibody A3C6E2 and then treated the same way as sample (2A).

Both samples were analyzed in a flow cytometer. The histograms obtained are given in FIGS. 2A–B. Both histograms show signals of equal intensity. This means that no internalization of the receptor occurred and that the antibody A3C6E2 according to the invention does not act as agonist, i.e. does not simulate the ligand, but has a strongly antagonistic (blocking) effect.

EXAMPLE 4

Use of the monoclonal antibody A3C6E2 for inhibiting the binding of SR-1

A sample (3A) of M07e cells was initially incubated with the antibody A3C6E2, and the bound antibody was then labeled with an anti-IgG1-PE antiserum.

A second sample (3B) of M07e cells was initially pre-incubated, for 30 minutes, with the known antibody SR-1 in a concentration of 10 µg/ml, and was then treated the same way as sample (3A) with the antibody A3C6E2 and the anti-IgG1-PE antiserum.

A third sample (3C) was initially pre-incubated, for 30 minutes, with the antibody A3C6E2 according to the invention, then incubated with the known antibody SR-1, and the bound SR-1 antibody was finally labeled with an anti-IgG2A-PE antiserum.

All three cell samples were analyzed in a flow cytometer. The histograms obtained are given in FIGS. 3A, 3B and 3C.

As is apparent from the histograms, binding of the antibody A3C6E2 was inhibited by the antibody SR-1 in sample (3B) to a degree of 94%, while binding of SR-1 was inhibited by A3C6E2 in sample (3C) to a degree of 98.7%.

These results show that both antibodies recognize the same or at least a very similar epitope on the SCF receptor protein CD117.

What is claimed is:

1. Hybridoma A3C6E2 (DSM 2247).

2. A monoclonal antibody produced by hybridoma A3C6E2 (DSM 2247).

3. A monoclonal antibody according to claim 2 linked to a detectable marker.

4. A monoclonal antibody according to claim 2 linked to a therapeutic reagent.

5. A composition comprising a monoclonal antibody according to claim 2 and a pharmaceutically acceptable carrier.

6. A composition comprising a monoclonal antibody according to claim 3 and a pharmaceutically acceptable carrier.

7. A composition comprising a monoclonal antibody according to claim 4 and a pharmaceutically acceptable carrier.

8. A method of detecting stem cell factor receptors, comprising the steps of
   (a) incubating a cell sample with a monoclonal antibody according to claim 2 under conditions which permit the binding of the antibody to the stem cell factor receptor; and
   (b) detecting antibody which is bound to stem cell factor receptors.

9. A method according to claim 8, wherein the cell sample comprises normal cells, leukemia cells, or lymphoma cells.

10. A method of detecting stem cell factor receptors, comprising the steps of
    (a) incubating a cell sample with a monoclonal antibody according to claim 3 under conditions which permit the binding of the antibody to the stem cell factor receptor; and
    (b) detecting antibody which is bound to stem cell factor receptors.

11. A method according to claim 10, wherein the cell sample comprises normal cells, leukemia cells, or lymphoma cells.

12. A method of isolating cells expressing the stem cell factor receptor, comprising the steps of
    (a) incubating a cell suspension with a monoclonal antibody according to claim 2 under conditions which permit the binding of the antibody to the stem cell factor receptor; and
    (b) separating cells bound to the antibody from those which are not bound to the antibody.

13. A method according to claim 12, wherein the cells are separated by column chromatography.

14. A method according to claim 12, wherein the cells are separated by fluorescence-activated cell sorting (FACS).

15. A method according to claim 12, wherein the cells are separated by immunoadsorption.

16. A method of transducing cells expressing stem cell factor receptor with a heterologous gene, comprising the steps of
    (a) isolating cells according to the method of claim 12; and
    (b) introducing a heterologous gene into said cells by means of a retroviral vector comprising the gene.

17. A method of separating normal cells from leukemic cells based upon differential expression of stem cell factor receptor, comprising the steps of
    (a) incubating a suspension comprising normal and leukemic cells with a monoclonal antibody according to claim 2 under conditions which permit the binding of the antibody to the stem cell factor receptor;
    (b) detecting antibody which is bound to stem cell factor receptors on said cells; and
    (c) separating cells to which a greater amount of the antibody is bound from cells to which a lesser amount of the antibody is bound.

18. A method of inhibiting hematopoiesis, comprising the step of contacting an antibody according to claim 2 with hematopoietic cells expressing stem cell factor receptor.

19. A method of inhibiting hematopoiesis, comprising the step of contacting an antibody according to claim 4 with hematopoietic cells expressing stem cell factor receptor.

20. A method of treating a patient suffering from a tumor, comprising the step of administering an antibody according to claim 2 to the patient in an amount effective to inhibit the growth or differentiation of the tumor cells.

21. A method of treating a patient suffering from a tumor, comprising the step of administering an antibody according to claim 4 to the patient in an amount effective to inhibit the growth or differentiation of the tumor cells.

22. A method for modifying the sensitivity of patients to cell cycle-specific chemotherapeutic agents, comprising the step of administering an antibody according to claim 2 to the patient in an amount effective to inhibit the growth and differentiation of cells within said patient which express stem cell factor receptor.

* * * * *